United States Patent [19]
Clark et al.

[11] Patent Number: 5,672,352
[45] Date of Patent: Sep. 30, 1997

[54] METHODS OF IDENTIFYING THE AVIAN REPELLENT EFFECTS OF A COMPOUND AND METHODS OF REPELLING BIRDS FROM MATERIALS SUSCEPTIBLE TO CONSUMPTION BY BIRDS

[75] Inventors: Larry Clark, Woodstown; J. Russell Mason, Bridgeton, both of N.J.; Pankaj S. Shah, Terre Haute, Ind.; Richard A. Dolbeer, Huron, Ohio

[73] Assignee: Monell Chemical Senses Center, Philadelphia, Pa.

[21] Appl. No.: 236,350

[22] Filed: May 2, 1994

Related U.S. Application Data

[63] Continuation-in-part of Ser. No. 102,855, Aug. 6, 1993, abandoned, which is a continuation of Ser. No. 836,054, Feb. 12, 1992, abandoned, which is a continuation-in-part of Ser. No. 679,432, Apr. 2, 1991, abandoned.

[51] Int. Cl.$^6$ .......................... A01N 25/28; A01N 25/02; A01N 25/04
[52] U.S. Cl. ........................ 424/405; 424/451; 424/40
[58] Field of Search ........................ 424/405, 451, 424/40

[56] References Cited

U.S. PATENT DOCUMENTS 2,967,128  1/1961  Kare.
4,790,990  12/1988  Mason et al..
5,187,196  2/1993  Cummings et al..

OTHER PUBLICATIONS

Budvari, S. (editor) "The Merck Index", 1989, pp. 68–69, Merck & Co., Inc.
Allen, C., "Mitigating impacts . . . Mine", McQuivey, R., coord. Proc. Nev. wildl./min. wrkshp Nev. Min. Assoc., Nev. Dept. Minerls & Nev. Dept. Wildl. 67–71 (1990).
Kay, F.R., "NDOW's role: past . . . future", McQuivey, R., coord. Proc. Nev. wildl./min. wrkshp Nev. min. Assoc., Nev.Dept.Minerls & Nev.Dept.Wildl.18–22 (1990).
Ohlendorf, N.M., et al.., "Nest success, . . . site", Condor 91:787–796 (1989).
Williams, M.L., et al., "Recruitment failure . . . Calif., 1984–1985", Condor 91:797–802 (1989).
Jackson, W.B. "Bird . . . Techniques." Pages 46–50, in R. McQuivey, coord.Proc.Nev.wildl./min. wrkshp. Nev. Min. Assoc., Nev. Dept. Minerals, & Nev. Dept. Wildl (1990).
Jakubas, W. & Guillon, "Coniferyl benzoate in quaking aspen a ruffed grouse feeding deterrent," J. Chem. Ecol. 16:1077–87 (1990).
Schroeder, M.L., "The Netting . . . Gold", pp. 72–81, in R. McQuivey, coord. Proc.Nev.wildl./min.wrkshop. Nev. Min. Assoc., Nev. Dept. Minerals & Nev. Dept. Wildl (1990).
Blokpoel, H., "Bird hazards to aircraft", Can. Wildl. Serv., Ottawa, Canada. 236 pp. (1976).
Besser, J.F., et al., "Baiting starlings with DRC–1339 at a cattle feedlot", J. Wildl. Manage. 31:48–51 (1967).
Palmer, T.X., "Pest bird damage . . . approach", pp. 177–21, Proc. Vertebr. Pest. Conf. Monterey, Calif (1976).
Feare, C.J., "The economics of starling damge", Econ of Dam 2:39–54 (1980).

(List continued on next page.)

Primary Examiner—Thurman K. Page
Attorney, Agent, or Firm—Woodcock Washburn Kurtz Mackiewicz & Norris LLP

[57] ABSTRACT

There is provided by the invention a structure-activity model for identifying avian repellent compounds. It has now been found that certain topological and electronic features of a molecule, especially the presence of a core ring structure, the basicity of the molecule in general, and the electronegativity of the core ring structure, are predictive of its avian repellency. Such features may be used to identify avian repellent compounds and such compounds may be utilized in methods for repelling birds from consuming or utilizing a material. There is further provided by this invention, novel avian repellents for use in methods of repelling birds from consuming or utilizing materials otherwise susceptible to consumption or utilization. Additionally, methods for repelling birds from consuming or utilizing non-potable aquatic habitats are provided herein.

25 Claims, 4 Drawing Sheets

OTHER PUBLICATIONS

Feare, C.J., et al. "Starling damge and its prevention at an open-fronted calf yard", *Anim. Prod.* 26: 259–265 (1978).

Glahn, J.F., et al., "dimethyl anthranilate as a bird repellent in livestock feed", *Wildl. Soc. Bull.* 17:313–320 (1989).

Mason, et al., "Anthranilate repellency to starlings: Chemical correlates and sensory perception," *J. Wildl Manage,* 53:55–64 (1989).

Szolscanyi, J., et al., "Nociception in pigeons is not impaired by capsaicin", *Pain* 27:247–260 (1986).

Mason, J.R. et al., "Exploitable . . . control", pp. 20–39 in D.E. Kaukienen,ed. *Vertb. pest cntrl & manag.matrls.* Am.Soc. for Test. & Matrls, Phila., Pa. pp. 315 (1983).

Dolbeer, et al., "Naphthalene shows no repellency for starlings," *Widl. Soc. Bull.* 16:62–64 (1988).

Mason & Otis, "Effectiveness of . . . (*Sturnus vulgaris*)," Chemical Senses, vol. 2, pp. 309–322 (Green, Mason & Kare, eds.), Marcel Dekker, Inc., N.Y. (1990).

Shah, et al., "Prediction of Avian . . . alcohol," *Pesticide Biochem and Physiol* 40:169–175 (1991).

Mason, et al., "Texon-specific differences . . . aversiveness," *J. Chem. Ecol.* 17:2539–51 (1991).

Clark, et al., "Chemical Repellency in Birds: Relationship between chemical structure and avoidance response," *J Exper Zool* 260:310–322 (1991).

Mason & Clark, "Nonlethal Avian Repellents: Current Status and Considerations for the Future," *Proc. Vert. Pest Conf.* 15–115–129 (1992).

Mason, J.R., et al. "Conditioned odor aversions in starlings " (*Sturnus vulgaris*), possibly mediated by nasotrigeminal cues *Brain Res.* 269:196–199 (1983).

Clark, L., et al., "Olfactory discrimination of plant volatiles by the European starling", *Anim. Behav.* 35:227–235 (1987).

Clark, L., et al., "Sensitivity of brown-headed cowbirds to volatiles", *Condor* 91:922–932 (1989).

Clark, L., et al., "Seasonal shifts in odor acuity by starlings", *J. Exp. Zool.* 255:22–29 (1990).

Clark, L., "Odor detection thresholds in tree swallows and cedar waxwings", *Auk* 108: 177–180 (1991).

Schuler, W., "responses to sugars and their behavioral mechanisms in the starlings" (*Sturnus vulgaris L.*), *Behavioral Ecol. and Sociobiology* 13:343–51 (1983).

Jakubas, et al., "Ruffed grouse feeding behavior and its relationship to the secondary metabolites of quaking aspen flower buds," *J. Chem. Ecol.* 15:1899–1917 (1989).

Clark & Mason, "Interactions between sensory and postingestional repellents in starlings: methyl anthranilate and sucrose," *Ecol. Appl.* 3:262–70 (1993).

Finger, et al., "Affecter and . . . cavity," *Chemical Senses,* vol. 2, pp. 1–18 (Green, Mason & Kare, eds.), Marcel Dekker, Inc., N.Y. (1990).

METHODS OF IDENTIFYING THE AVIAN REPELLENT EFFECTS OF A COMPOUND AND METHODS OF REPELLING BIRDS FROM MATERIALS SUSCEPTIBLE TO CONSUMPTION BY BIRDS

CROSS REFERENCE TO RELATED APPLICATIONS

This is a continuation-in-part of application Ser. No. 08/102,855, filed Aug. 6, 1993, now abandoned which is a continuation of application Ser. No. 07/836,054, filed Feb. 12, 1992, now abandoned which is a continuation-in-part of application Ser. No. 07/679,432, filed Apr. 2, 1991, now abandoned.

FIELD OF THE INVENTION

This invention relates to methods for repelling birds from consuming or utilizing materials otherwise susceptible to consumption or utilization by birds, including methods for repelling birds from consuming or utilizing non-potable water. The invention also relates to methods of predicting the avian aversive characteristics of compounds.

BACKGROUND OF THE INVENTION

Industrial applications for wastewater impoundments.

Growing human populations place increasing demands on agriculture and industry. Processes from industry and agriculture often produce by-products, such as waste water, which must be stored in impoundments until it can be safely processed. While these impoundments may meet Federal and State regulations pertaining to protection of groundwater, they often pose an inherent risk to wildlife. Allen, C., "Mitigating impacts to wildlife at FMC Gold Company's Paradise Peak Mine", McQuivey, R., coord. Proc. Nev. wildl./mining workshop Nev. Mining Assoc., Nev. Dept. Minerals, and Nev. Dept. Wildl. 67–71 (1990); Kay, F. R., "NDOW's role: past, present, future", ibid 18–22 (1990). Waterfowl and other game species are often attracted to such freestanding water. Should the wildlife drink from impoundments, they risk death or exposure to the bioaccumulation of toxic substances, e.g. heavy metals and mutagens.

There is ample evidence to indicate that bioaccumulation of toxicants can decrease the reproductive capacity of waterfowl, and hence negatively affect wildlife populations. Ohlendorf, N. M., et al., "Nest success, cause-specific nest failure, and hatchability of aquatic birds at selenium-contaminated Kesterson Reservoir and a reference site", Condor 91:787–796 (1989); Williams, M. L., et al., "Recruitment failure in American avocets and black-necked stilts nesting at Kesterson Reservoir, California, 1984–1985", Condor 91:797–802 (1989). However, even if the actual impact of impoundments on wildlife populations is negligible, protection of wildlife is an important issue. For example, the Migratory Bird Treaty Act (16 U.S.C. § 703–711) sets zero tolerance for bird mortality. See also, Lacey Act, 18 U.S.C. § 42–44; Black Bass Act, 16 U.S.C. § 851–856; Bald Eagle Protection Act, 16 U.S.C. §§ 668–668d; Tariff Classification Act of 1962, 19 U.S.C. § 1202, (Schedule 1, Part 15D, Headnote 2, T.S.U.S.); Endangered Species Conservation Act of 1969, 16 U.S.C. §§ 668aa–668cc-6). The U.S. Fish and Wildlife Service has targeted the mining and petroleum industries for enforcement in an attempt to eliminate the attractive nuisance that wastewater ponds represent to birds, and to bring these industries in compliance with the Migratory Bird Treaty Act. However, traditional hazing methods are ineffective at achieving zero mortality. (Kay, supra (1990); Jackson, W. B. "Bird Repelling Techniques". Pages 46–50. in R. McQuivey, coord. Proc. Nev. wildl./mining workshop. Nev. Mining Assoc., Nev. Dept. Minerals, and Nev. Dept. Wildl (1990). The only current commercially available effective means of preventing wildlife from using ponds is exclusion by netting. Because wastewater ponds typically range from 1 to 400 acres, this option is often impractical. For example, FMC Gold Company, spent $8 million (in netting) at the Paradise Peak Mine to exclude waterfowl; this investment resulted in reducing avian mortality from 1,548 in 1986–87 to 88 in 1988–89. Allen, C., supra, *Department of Wildlife, State of Nevada Statistics on bird mortality* (1990). The inability to reduce mortality to zero reflects the failure of netting under variable and severe weather conditions. Thus, despite substantial reductions in avian mortality, the results of attempted exclosure still do not meet the requirements set forth by the U.S. Fish and Wildlife Service.

Other means of protecting wildlife are also expensive. For example, the gold/silver mining industries, in which U.S. sales were over $3.3 billion for 1989, use cyanide to extract heavy metals from ore. Because cyanide is used, the leachate impoundments are highly toxic to wildlife. Eliminating the cyanide used in the mining industries from ponds via quenching may cost $240–400,000/year for a mid sized operation. Excluding birds from ponds until cyanide reclamation or quenching can be achieved is also costly, running between $9–13,000/acre, resulting in costs of $36–404,000 for a range of pond sizes from 3 to 45 acres. Schroeder, M. L., "The netting of cyanide ponds at Copperstone Gold", Pages 72–81. in R. McQuivey, coord. Proc. Nev. wildl./ mining workshop. Nev. Mining Assoc., Nev. Dept. Minerals, and Nev. Dept. Wildl (1990). Further, quenching is often not desirable because cyanide can be recovered and used again.

Economic figures for the petroleum industry and agriculture wastewater drainage basins are not readily available. It is clear, however, that wastewater negatively impacts wildlife. Successful breeding at agriculturally contaminated sites has all but ceased due to bioaccumulation of selenium in eggs. Ohlendorf, H. M., et al., supra, (1989). The U.S. Fish and Wildlife Service is seeking methods to discourage birds from breeding at the contaminated reservoirs. Methods proposed have been as drastic as poisoning the aquatic invertebrate communities in the reservoir so as to eliminate bird food resources. To date, no method has been effective.

It is clear from the above data that birds are at risk when they come in contact with wastewater. It is also clear that industry and agriculture have a substantial investment to protect. However, the only current commercially available effective means of preventing wildlife from utilizing wastewater ponds (exclusion by netting) is often impractical. There is a need to develop an economical alternative or ancillary strategy for repelling birds from consuming or utilizing non-potable water that may not be suitable for nutritive purposes or sustenance. Certain embodiments of the present invention relate to materials and methods for dissuading birds from consuming or otherwise utilizing industrial or agricultural wastewater. This invention discloses, inter alia, methods whereby consumption of wastewater is reduced to zero, or to levels within the toxicological tolerance of avian species.

Aviation industry and application to free-standing freshwater.

An additional area of conflict between wildlife and humans arises at airports. Gulls, waterfowl and other species frequently flock to temporary pools of fresh water at airports after heavy rains, creating safety hazards for aircraft. Blokpoel, H., "Bird hazards to aircraft", Can. Wildl. Serv., Ottawa, Canada. 236 pp. (1976). Many airports report numerous airstrikes with birds. Birds are often attracted to airports after rains because of the freestanding water which accumulates on tarmacks and runways. In 1989, the economic losses to the U.S. military operations were on the order of $80 million. Civilian losses were reported to be a minimum of $100 million (USDA-FAA liaison office, Atlantic City). As is the case in mining operations, traditional hazing techniques are ineffective. The birds are only moved from one location to another near the airport or soon become habituated to the hazing. The goal is to dissuade the birds from using the airport at all. Currently, there are no practical methods for decreasing avian utilization of non-potable water pools formed after rain storms or after irrigation. There is a need to develop a practical strategy for repelling birds from consuming or utilizing such non-potable water. Certain embodiments of the present invention relate to materials and methods for reducing avian consumption or utilization of non-potable water pools.

Edible additives and agricultural applications.

Blackbirds and starlings (Sturnus vulgaris) can cause significant feed loss seasonally at cattle and swine operations, with the larger feedlots suffering the most damage. See e.g., Besser, J. F., et al., "Baiting starlings with DRC-1339 at a cattle feedlot", J. Wildl. Manage. 31:48–51 (1967); Palmer, T. X., "Pest bird damage control in cattle feedlots: the integrated systems approach", Proc. Vertebr. Pest. Conf. Monterey, Calif. (1976); Feare, C. J., "The economics of starling damage", Econ of Dam 2:39–54 (1980). Estimates of the grain component of feed lost to birds ranges from 10–12%. Feare, C. J., et al. "Starling damage and its prevention at an open-fronted calf yard", Anim. Prod. 26:259–265 (1978). The risk of avian feedlot depredation to individual farmers is significant. Twenty-six percent of farmers in Tennessee reported more than negligible damage, with 6% reporting significant losses of feed to birds. Glahn, J. F., et al., "Dimethyl anthranilate as a bird repellent in livestock feed", Wildl. Soc. Bull. 17:313–320 (1989). Use of repellents to reduce consumption would be beneficial if costs of the repellent could be kept below 10% of the cost of the feed.

Birds also cause significant damage to livestock by transmitting disease. For example, over 10,000 pigs were lost to gastroenteritis during the winter of 1978–79 in one county in Nebraska. Although the total number of swine and cattle farms in not readily available for the U.S., it is clear that the potential economic loss of stock through transmissible disease is large. Certain embodiments of the present invention relate to materials and methods for reducing livestock losses due to certain avian species.

Birds also cause significant damage to crops. Currently, there is a need to develop non-lethal bird repellents to control avian crop depredation and accidental bird poisonings. Mason, et al., "Anthranilate repellency to starlings: Chemical correlates and sensory perception," J. Wildl Manage, 53:55–64 (1989). Certain embodiments of the present invention relate to materials and methods for reducing crop losses due to certain avian species.

Sensory Biology of Birds.

Repellency in birds is substantially different than that in mammals. Szolscanyi, J., et al., "Nociception in pigeons is not impaired by capsaicin", Pain 27:247–260 (1986); Mason, J. R., et al., "Exploitable characteristics of neophobia and food aversions for improvements in rodent and bird control", Pages 20–39 in D. E. Kaukienen, ed. Vertebrate pest control and management materials. Am. Soc. for Testing and Materials, Philadelphia, Pa. 315 pp (1983). Although there is evidence that irritants are perceived similarly within a vertebrate class, there are dramatic differences in perception between classes. Birds do not avoid familiar mammalian irritants such as ammonia, gingerol, zingerone, hydroquinones, naphthalene. Dolbeer, et al., "Naphthalene shows no repellency for starlings," Widl. Soc. Bull. 16:62–64 (1988); Mason & Otis, "Effectiveness of six potential irritants on consumption by red-winged blackbirds (Agelaius phoeniceus) and starlings (Sturnus vulgaris)," Chemical Senses, vol. 2, pp. 309–22 (Green, Mason & Kare, eds.), Marcel Dekker, Inc., N.Y. (1990). Other mammalian irritants, such as piperine, allyl isothiocyanate and mercaptobenzoic acid, have some repellent effects, but only at high concentrations (>10,000 ppm) under specific presentation schemes. Mason & Otis, supra (1990). The most striking example of the difference between birds and mammals is for capsaicin. Mammals uniformly avoid capsaicin (the hotness in red chilies) at about 100–1000 ppm. Birds will readily consume up to 20,000 ppm. Solzcsanyi, et al., "Nociception in pigeons is not impaired by capsaicin," Pain 27:247–60 (1986); Mason, et al., "Taxon-specific differences in responsiveness to capsaicin and several analogues: correlates between chemical structure and behavioral aversiveness," J. Chem. Ecol. 17:2539–51 (1991).

Avoidance of a compound can be based on postingestional factors, e.g., toxicity, where a conditioned aversion to a sensory cue is learned. Avoidance can also be mediated via purely sensory cues. Clark, et al., "Chemical Repellency in Birds: Relationship between chemical structure and avoidance response," J Exper Zool 260:310–322 (1991). Methyl and dimethyl anthranilate (MA and DMA, respectively) are ester derivatives of anthranilic acid. MA, DMA and other ester derivatives of anthranilic acid as well as esters of phenylacetic acid, have been shown to be effective bird repellents with preferred embodiments as feed additives to deter feed loss (U.S. Pat. Nos. 2,967,128 and 4,790,990) and as anti-grazing compound for geese and swans (Mason, J. R., supra, (1989)). That olfaction and trigeminal chemoreception underlie the aversiveness of methyl and dimethyl anthranilate to birds (Mason, J. R., et al., "Anthranilate repellency to starlings: chemical correlates and sensory perception" J. Wildl. Manage 53:55–64 (1989)), suggests that avoidance is based upon odor quality and irritation. These findings are in sharp contrast to earlier findings claiming that the limited taste capacities of birds mediated repellency. Recent findings indicate that birds are fully capable of making quantitative and qualitative odor discriminations. Mason, J. R., et al. "Conditioned odor aversions in starlings (Sturnus vulgaris), possibly mediated by nasotrigeminal cues", Brain Res. 269:196–199 (1983); Mason, J. R., et al , supra, (1989); Clark, L., et al., "Olfactory discrimination of plant volatiles by the European starling", Anim. Behav. 35:227–235 (1987); Clark, L., et al., "Sensitivity of brown-headed cowbirds to volatiles" Condor 91:922–932 (1989); Clark, L., et al., "Seasonal shifts in odor acuity by starlings", J. Exp. Zool. 255:22–29 (1990); Clark, L., "Odor detection thresholds in tree swallows and cedar waxwings", Auk 108:177–180 (1991). Indeed, many birds avoid edibles based upon chemosensory cues. Schuler, W., "Responses to sugars and their behavioral mechanisms in the starlings" (Sturnus vulgaris), Behavioral Ecol. and Sociobiology 3:243–51 (1983); Mason, et al., "Anthranilate repellency to starlings: chemical correlates and sensory perception," J. Widl. Manage. 53:55–64 (1989). When avoidance is nonlearned and resistant to habituation, the bird is most likely responding to a chemical irritant. Clark & Mason, "Interactions between sensory and postingestional repellents in starlings: methyl anthranilate and sucrose," *Ecol. Appl.* 3:262–70 (1993). Mediation of irritation is via the chemically sensitive fibers (A and C fibers) of the trigeminal nerve. Finger, et al., "Affecter and effector functions of peptidergic innervation of the nasal cavity," *Chemical Senses*, vol. 2, pp. 1–18 (Green, Mason & Kare, eds.), Marcel Dekker, Inc., N.Y. (1990). These fibers are typically found in the highest densities around mucous membranes; for birds, this corresponds to the eyes and buccal and nasal cavities.

Current Need for Avian Repellents.

Although MA and DMA have been shown to repel birds from edibles, not all of the ester derivatives of anthranilic acid are repellent to birds. For example, linalyl anthranilate is a good repellent, Whereas phenethyl anthranilate, a compound with the same molecular weight, is not repellent. Clark, et al., supra, (1991). These data suggest that isomerization is not the only important factor in identifying bird repellent compounds.

Further, a simple aqueous emulsion of DMA sprayed on food lacks sufficient taste persistency to serve as an economically attractive taste aversive agent. U.S. Pat. No. 4,791,990. Although emulsion in a liquid other than water may increase taste persistency and thereby increase avian aversiveness, it is suggested that once evaporation of the emulsive agent occurs, flavor persistency will rapidly decrease. Further, DMA is light sensitive and will degrade to a noneffective form in sunlight without adequate protection. Thus, although the avian repellent properties of certain anthranilic esters have been recognized, such esters have been used only for repelling birds from edibles. Ecologically sound avian repellents have numerous advantages. For example, coniferyl benzoate, a compound found in quaking aspen (*Populus tremuloides* Michx), is an important factor mediating ruffed grouse food selection. Jakubas, W. & Guillon, "Coniferyl benzoate in quaking aspen a ruffed grouse feeding deterrent," *J. Chem. Ecol.* 16:1077–87 (1990); Jakubas, et al., "Ruffed grouse feeding behavior and its relationship to the secondary metabolites of quaking aspen flower buds," *J. Chem. Ecol.* 15:1899–1917 (1989). However, there is a need to identify naturally occurring compounds that would repel omnivorous birds such as starlings. There is an interest in bird repellents that pose little or no environmental risk due to a low potential for bioaccumulation and a specific biological action. The paramount advantage is that the birds can be kept away from crops or other materials while not increasing mortality risk due to exposure to the repellent. There is a further need for bird repellent chemicals that serve as safe repellent additives to agricultural products or standing water and that might serve as safe sprayable repellents for use on crops. Such repellents are preferred because agriculture, industry and wildlife interests would be met. If used to reduce wildlife hazards associated with formulated agricultural chemicals, the ecologically sound avian repellant also could have an enormous economic impact, particularly on major American chemical producers, and the farmers who rely on the continued availability of the producer's agricultural products. Mason & Clark, "Nonlethal Avian Repellents: Current Status and Considerations for the Future," *Proc. Vert. Pest Conf.* 15:115–129 (1992).

Despite increasing demand, few non-lethal chemicals (i.e., repellents) are available for the control of avian depredation and nuisance problems. Mason and Clark, supra (1992). Until now the small number of compounds known in the art to be capable of repelling birds from consuming or utilizing materials otherwise susceptible to consumption or utilization by birds, were identified empirically without recognition of the underlying principles taught herein. There is a need for a method of predicting the avian repellency of a compound. Certain embodiments of the present invention relate to methods for predicting the avian repellency of a compound. The invention has considerable value in that it adds novel avian repellents and allows identification of additional novel avian repellents to be added to the small list of chemicals known to effectively repel birds from consuming or utilizing materials susceptible to consumption or utilization by birds. As such, the invention represents a significant contribution to improved agricultural technology, and fulfills a technological need.

Further provided by this invention are methods of repelling birds from non-potable water. Currently, there are no chemicals commercially available to prevent the accidental ingestion of pelleted agricultural chemicals, treated seeds, agricultural wastewater, or the toxic solutions found in industrial evaporating ponds. Shah, et al., "Prediction of Avian Repellency from Chemical Structure: The aversiveness of vanillin, vanillyl alcohol, and veratryl alcohol," *Pesticide Biochem and Physiol* 40:169–175 (1991).

Additionally, if used to reduce the non-target hazards associated with mammalian toxicants and agrichemicals, the invention could have a substantial positive environmental impact. If used to reduce wildlife hazards associated with formulated agricultural chemicals, the invention could have an enormous economic impact, particularly on major American chemical producers, and the farmers who rely on the continued availability of the producer's agricultural products.

OBJECTS OF THE INVENTION

It is an object of this invention to provide novel avian repellents and methods of repelling birds from consuming or utilizing a material otherwise susceptible to consumption or utilization by birds.

It is a further object of this invention to provide methods for repelling birds from consuming or utilizing non-potable water.

It is still a further object of this invention to provide methods for predicting the avian repellency of a compound, and for using the compounds identified in such methods to repel birds from consuming or utilizing a material.

These and other objects of the present invention will be apparent from a review of the instant specification and attendant claims.

SUMMARY OF THE INVENTION

It has now been found that certain topological and electronic features of a molecule, especially the presence of a core aromatic structure, such as a benzene, thiazole or thiol ring, the basicity of the molecule in general, and the electronegativity of the core aromatic structure, are predictive of its avian repellency. In certain embodiments of the present invention, such features are used to identify compounds capable of repelling birds from consuming or utilizing a material otherwise susceptible to consumption or utilization by birds. In other embodiments of this invention, avian repellent compounds identified by such methods are used in methods for repelling birds from consuming or utilizing a material otherwise susceptible to consumption or utilization by birds.

There is further provided by this invention, novel avian repellents for use in methods of repelling birds from consuming or utilizing materials otherwise susceptible to consumption or utilization. In such methods, an avian repellent amount of at least one such compound is provided to the material from which birds are to be repelled.

This invention further provides methods for repelling birds from consuming or utilizing non-potable aquatic habitats, comprising providing to the aquatic habitat an avian repellent amount of at least one anthranilic ester.

DETAILED DESCRIPTION OF THE INVENTION

Figure 1A:
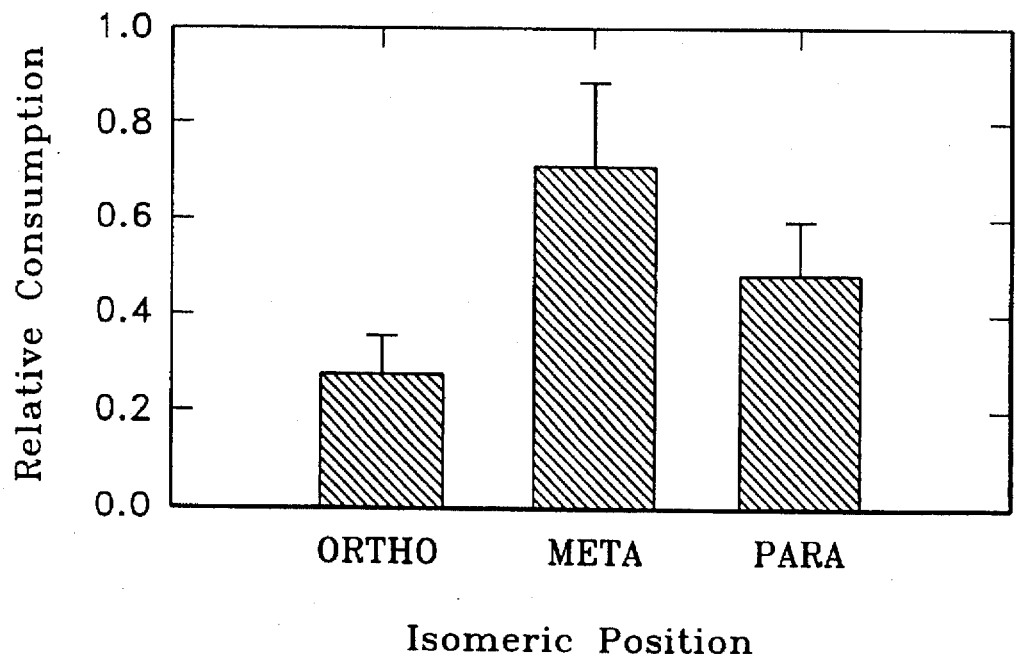
FIG. 1. (A) Ranking of relative water consumption as a function of isomeric position of the electron donating group. Ortho and para isomers are capable of resonance of lone electron pairs, the meta isomers are not. Consumption is relative to consumption of water controls. (B) Ranking of relative water consumption as a function of basicity of the molecule. Amino substituents are the most basic; hydroxy substituents are the least basic. (C) Ranking of relative water consumption as a function of the presence or absence of intramolecular hydrogen (H) bonding.

Heretofore, avian repellents have been identified empirically. It has now been found that certain topological and electronic features of a molecule, especially the presence of a core aromatic structure, are predictive of its avian repellency. The core ring structures may be N—, S—, or O— substituted five or six ring structures in addition to being a phenyl ring, as long as the ring is unsaturated. An unsaturated structure should be electron rich (basic) and have resonance. Those molecules that maximize the charge gradient between the electron withdrawing and donating groups are good repellents, whereas acidification, especially within electron withdrawing groups and delocalization of lone pairs of electrons hinders repellency. Those molecules that have electron withdrawing groups conjugated in the same plane as the aromatic ring structure are better repellents, whereas electron withdrawing substituents that are not conjugated are not repellent.

In certain embodiments of the present invention, the structure-activity model provided herein is used in methods of identifying avian repellent compounds. In such methods, a compound having one of the following core structures

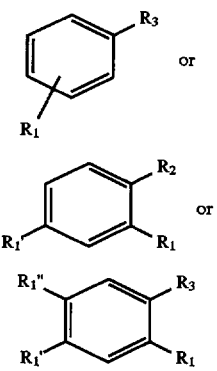

wherein $R_1$ or $R_{1'}$ or $R_{1''}$ is an electron donating group and $R_2$ is an electron withdrawing group or a neutral group which group does not substantially hinder electron donation to the core ring structure by $R_1$, is selected and optionally tested to confirm its repellency.

Electron donating groups are well known to those skilled in the art and a variety of suitable examples include amine, o-lower alkyl, N-lower alkyl, and N-di lower alkyl. Specific examples would include $NH_2$, $NHCH_3$, $NC_2H_6$, $NHOC_2H_5$ and $OCH_3$.

With respect to the substituents on the core ring structure, it is preferred that $R_2$ is an electron withdrawing group (EWG) and/or $R_2$ is a group capable of forming a hydrogen bonded ring structure with an electron donating group, $R_1$. Both types of $R_2$ groups are well known to those in the art and a variety of examples of such groups are shown herein and include lower acyl, carboxylic acids, esters and nitro groups as examples of electron withdrawing groups. The other type includes groups like $CH_2$ and $CH_2NH_2$. Specific examples for $R_2$ include $COCH_3$, $COOCH_3$, $COOC_2H_5$, $COOC_2H_4$-phenyl, COO-linalyl, $NO_2$, $CH_2OH$ and $COCH_2NH_2$. Thus, $R_2$ can be of two forms, an EWG or not. If it is an EWG, then in association with an $R_1$ at positions 2 and 4 resonance can occur and this contributes to repellency. $R_2$ may also contribute to repellency even if it is not an EWG, however it should form a hydrogen bonded ring structure with $R_1$, e.g., 2-aminobenzyl alcohol; or an electron donating group within itself, e.g, alpha-aminoacetophenone. And it is preferred that the substituents on $R_2$ are of the type that do not substantially prevent $R_1$ from donating electrons to the core ring structure, e.g., phenethyl anthranilate (probable stearic effects) or isotonic anhydride (electronic effects).

It is preferred that the electron donating groups, $R_1$ or $R_{1'}$ or $R_{1''}$ contribute electrons to the core ring structure, most preferably in position 2, 3 or 4 with respect to $R_2$. It is also preferred that the electron donating group is basic. Additionally, it is preferred that there is intramolecular hydrogen bonding between $R_1$ and $R_2$ when $R_1$ is in position 2 relative to $R_2$, e.g., ortho-aminoacetophenone or 2-hydroxyacetophenone.

$R_1$ and $R_2$ may comprise a heterocyclic ring attached to the core ring structure such as 4-keto benztriazine.

That these core structures, topological and electronic features are predictive of the avian repellency of a compound is unexpected in view of the prior art. For example, Kare (U.S. Pat. No. 2,967,128) teaches that substitution on the phenyl ring of an acetate will decrease repellent action of the compound. It has now been found that substitution on the phenyl ring is important as it relates to electron donating and withdrawing capacity; substitutions which preserve electron richness of the phenyl ring will yield better repellency than those that act to deplete ring electron richness.

That these core structures, topological and electronic features are predictive of the avian repellency of a compound is also unexpected in view of Mason, Adams and Clark, "Anthranilate repellency to starlings: Chemical correlates and sensory perception," *J. Wildlife Management* 53:55-64 (1989). Based on a systematic study of anthranilates, Mason, et al., concluded that lipophilicity (the ease with which a molecule can dissolve in a nonpolar solvent, i.e., fat) was a critical predictor of repellency. However, the data provided herein is not consistent with this. For example, methyl anthranilate (MA), which has a partition coefficient (an index of lipophilicity) of 83, is much less repellent than ortho-aminoacetophenone (OAP), which has a partition coefficient of 40. While OAP is only half as soluble in nonpolar solvents relative to MA, OAP is an order of magnitude more effective as a repellent.

The structure-activity model taught herein for identifying avian repellent compounds is a significant advancement in the art that not only facilitates identification of novel avian repellents, but also accounts for differences in effectiveness of different isomers. This model advances the understanding of stereographic, electronic, and topological attributes of chemicals considerably beyond consideration of empirical formulas.

For example, from the data provided herein, it is apparent that not all isomers of an avian repellent compound are repellent. Simple substitution does not lead to an equal likelihood of repellency. For example, 2-hydroxyacetophenone is a repellent hydroxyacetophenone isomer, whereas 3-hydroxyacetophenone and 4-hydroxyacetophenone are not repellent. Similarly, 2-aminobenzoic acid (anthranilic acid) is repellent whereas 3-aminobenzoic acid and 4-aminobenzoic acid are not. Further, methyl anthranilate, ethyl anthranilate, N-dimethyl anthranilate, linalyl anthranilate, proplonyl methyl anthranilate and menthyl anthranilate are repellent whereas isobutyl anthranilate, isobutyl methyl anthranilate, isobutyl-N,N-dimethyl anthranilate, and phenyl ethyl anthranilate are not repellent. Additionally, aromatics containing heterocyclic structures, such as isoquinoline, benzothiole, indole, and 2-actyl thiozole are good repellents, however, not all pyroles, thioles thiazoles or quinonline structures are repellent; only those which meet the stereochemical and electronic attributes of the structure-activity model disclosed herein are repellent.

Generally, the nonrepellent isomers for a given moiety delocalize the lone pair of electrons to a greater extent than observed for the repellent structures. Isomeric position of the electron donating substituent which leads to resonance of lone pairs of electrons is an important feature of repellency; i.e., repellency is enhanced when electron donating substituents are in the ortho and para positions. An ancillary contributory factor enhancing repellency is believed to be the presence of intramolecular hydrogen bonds. Combining these features appears to improve repellency.

One aspect of this invention provides methods for repelling birds from consuming or utilizing a material otherwise susceptible to consumption or utilization by birds, comprising providing to the material an avian repellent amount of at least one compound selected from the group comprising alpha-aminoacetophenone, ortho-aminoacetophenone, meta-aminoacetophenone, para-minoacetophenone, ortho-hydroxyacetophenone, ortho-methoxyacetophenone, meta-methoxyacetophenone, para-methoxyacetophenone, anthranilic acid, 3-aminobenzoic acid, 4-aminobenzoic acid, 4-ketobenztriazine, coniferyl benzoate, cinnamyl benzoate, 3-4-dimethoxycinnamyl benzoate, coniferyl alcohol, cinnamyl alcohol, 3-4dimethoxycinnamyl alcohol, acetophenone, 2-amino-4,5-dimethoxyacetophenone, methyl-2-methoxybenzoate, methyl-4-methoxybenzoate, methyl benzoate, anthranil, 2-aminobenzyl alcohol, N,N-dimethyl aniline, ethyl phenyl acetate, methyl phenyl acetate, phenethyl alcohol, benzaldehyde, salicylaldehyde, o-tolualdehyde, o-anisaldehyde, pyrole, pyridine, pyrazine, indol, peperazine, isoquinoline, benzothiole, 5,6,7,8-tetrahydroisoquinoline, 2-acetylthiazole, 2-acetyl thiophene, thiazole, and tetrahydroquinoline.

These compounds are chemically and physiochemically distinct. For example, acetophenones, quinolines, triazines, pyroles, pyridines, pyrazines, and thiophenes are all distinct classes of chemicals with differing physiochemical properties. However, these novel avian repellents have features consistent with the structure-activity model taught herein.

In the practice of certain embodiments of the present invention, these compounds may be applied to the material from which birds are to be repelled in any suitable manner. For example, liquid carriers may be employed and the repellent may be sprayed on the material. See e.g. U.S. Pat. No. 2,967,128 which patent is incorporated by reference as if fully set forth herein. The compound may be dispersed in the liquid from which the birds are to be repelled. The repellent may be at least partially trapped in a solid vehicle to improve its persistency such as disclosed in U.S. Pat. No. 4,790,990 which patent is incorporated by reference as if fully set forth herein. The vehicle may be a modified starch, oil or polymer which at least partially encapsulates, emulsifies or substantially uniformly disperses the aversive agent. The repellent compound and vehicle may be dispersed throughout solids consumed by avian species to reduce the likelihood that they will eat the treated edible.

Certain embodiments of the present invention are directed to methods of repelling birds from consuming or utilizing non-potable liquids such as industrial or agricultural waste water, mine tailing ponds, and freestanding water on artificial surfaces like airport runways and parking lots. "Non-potable" refers to liquids or aquatic habitats wherein said liquid may be consumed or utilized by birds to the detriment of man or the birds.

Previously it has been shown, in U.S. Pat. Nos. 2,697,128 and 4,790,990, that dimethyl anthranilate (DMA) and methyl anthranilate (MA) are repellents for some avian species when incorporated in or sprayed on foodlots or food crops. In U.S. Pat. No. 5,187,196, it was disclosed that DMA and MA may be used to repel geese and swans from habitats for such birds. However, a simple aqueous emulsion of dimethyl anthranilate sprayed on food lacks sufficient flavor persistency to serve as an economically attractive flavor aversive agent. U.S. Pat. No. 4,791,990. Further, DMA is light sensitive and will degrade to a noneffective form in sunlight without adequate protection. Surprisingly, waste water derived from pond tailings is actually preferred relative to deionized distilled water by birds. It has now been unexpectedly discovered that treatment with at least one anthranilic ester, such as MA, DMA, or a combination thereof, synergistically decreases consumption beyond what one would expect based on treatment of deionized, distilled water.

In the embodiments of the present invention that provide methods for repelling birds from consuming or utilizing non-potable water, an avian repellent amount of at least one anthranilic ester, such as MA or DMA or mixtures thereof, is provided to such non-potable water. The anthranilic ester(s) may be provided to the non-potable water in any suitable manner. For example, the anthranilic ester(s) may be dispersed in the non-potable water, or may be provided to the non-potable water by liquid or solid carrier, such as a starch, oil or polymer which at least partially encapsulates, emulsifies or substantially disperses the anthranilic ester(s) in the non-potable water.

At least one anthranilic ester may be dispersed in the liquid to reduce the amount of liquid consumed by avian species, and to reduce the likelihood that birds will rest or swim in the liquid. The anthranilic ester(s) may be incorporated into freestanding water, industrial or agricultural wastewater or fluid toxic containment ponds to reduce the likelihood that birds will drink, rest or swim in the liquid, resulting in reduced mortality and morbidity to birds. The anthranilic ester may also be incorporated into a polymer to reduce the likelyhood that birds will ingest or otherwise orally manipulate the treated polymer.

As used herein, the term "birds" refers to members of the class "Aves".

As used herein, "utilization" refers to contact by the bird. Such utilizations that may be repelled include, for example, bill dipping or swimming in contaminated waters, and landings on a variety of hazardous surfaces such as runways and parking lots.

"Materials" from which birds are to be repelled from consuming or utilizing, as used herein, refers to materials otherwise susceptible to consumption or utilization by birds. Examples include edible and non-edible materials such as water, feeds, crops, waste waters, seeds, polymer surface coatings, and agrichemicals such as pesticides and herbicides. Those skilled in the art will recognize other materials which would benefit from the methods of this invention.

A compound is an "avian repellent compound" if it is capable of repelling birds from consuming or utilizing a material otherwise susceptible to consumption or utilization by birds.

An "avian repellent amount" suitable for use in the methods of this invention is that amount effective to reduce the amount of consumption or utilization of the material by birds. This amount can be easily determined by methods known to those skilled in the art. For example, one can test to determine the amount of compound necessary to achieve repellency similar to repellency of known repellents on the same type of material. Such testing may involve testing a series of concentrations to determine the amount of compound that provides the desired repellency for the material to which it is to be applied. Generally, compounds are used in an amount to provide at least about 0.001 to 1% v/v or w/v of said compound.

Birds are repelled from a material when utilization or consumption of the material by birds is reduced. In the methods for repelling birds from consuming or utilizing a material otherwise susceptible to consumption or utilization at least one compound is utilized that reduces the amount of consumption or utilization of a material by birds as compared to consumption or utilization by birds in the absence of the compound.

In preferred embodiments, the avian repellent amount of compound is that amount sufficient to reduce the consumption or utilization of said material by said birds to at least about fifty percent (50%) (and most preferably at least about ninety percent (90%)) as compared to the amount of said material which would otherwise be consumed or utilized by said birds in the absence of said compound.

The compounds disclosed herein are available from a variety of commercial sources, such as, for example, Aldrich Chemical Co., Milwaukee, Wis., and PMC, Specialties, Cincinnati, Ohio.

Methods to test compounds to confirm their ability to repel are known to those in the art and several are detailed in the Examples. Briefly, one suitable test comprises comparing the consumption or utilization by a bird of a material with the consumption or utilization by a bird of the same material to which an avian repellent compound has been provided, whereby a reduction in consumption of the material with said compound confirms the ability of said compound to repel birds from consuming or utilizing materials susceptible to consumption or utilization by birds. For example, a compound which when provided to a material decreases avian utilization or consumption of that material by a statistically significant amount as compared to avian consumption or utilization of the same material in the absence of the compound, the avian repellency of the compound is confirmed. Statistical significance may be judged by appropriate statistical tests, including but not limited to a t-statistic or analysis of variance, relative to a plain water control at a probability level of 0.05 or less.

Variations and modifications of the aforementioned can, of course, be made without departing from the spirit and scope of the invention as disclosed herein, and those skilled in the art will recognize multiple utilizations of the present invention that are within the scope of this disclosure.

EXAMPLES

Materials and Methods

DRINKING ASSAYS

Procedure.

Starlings (*Sturnus vulgaris*) were chosen as test animals because previous experiments showed them to be good models of avian sensitivity (Clark and Shah 1991). Starlings were individually caged (61×36×41 cm) under a 12:12 light:dark cycle for at least a two week adaptation period and given free access to Purina Flight Bird Conditioner (Purina Mills, St. Louis, Mo.), water and oyster shell grit (United Volunteer Aviaries, Nashville, Ten.). Capture, maintenance, and experimental protocol were carried out in compliance with guidelines set forth by the Institutional Animal Care Committee.

The experimental design utilized a standard drinking assay (Clark and Shah 1991), and consisted of an adaptation/assignment and treatment phase.

During the adaptation/assignment phase, birds were presented with tap water contained within calibrated drinking tubes for each of five days. Water intake was recorded every two hours for a total of six hours, after which the graduated tubes were replaced with standard water bottles. Starlings (n=36) were ranked on the basis of mean water consumption and assigned to one of six groups in a counter-balanced fashion. Similarity for water consumption among groups was validated using a one-way analysis of variance (1-way anova), and was a prerequisite for further testing. Groups were next randomly assigned to receive one of six concentrations of a single compound.

During the treatment phase, groups were presented with one of six concentrations of test repellent and fluid intake was monitored every two hours for a total of six hours. Total consumption was noted and divided by that individual's pretreatment water consumption. This ratio is called the repellency index. Data were tested for normality and variances for heterogeneity. Treatment and concentration effects were analyzed using a repeated measures, 2-way analysis of variance. Post-hoc tests were evaluated using a Duncan's multiple range test. Statistical significance was assumed if the probability for each test was, $P<0.05$.

FEEDING TRIALS

Procedure.

Two-cup tests. The procedures detailed in Mason et al., supra, (1989) for 2-cup avian repellency evaluations were followed. Briefly, for each isomer, starlings were randomly selected, weighed, and then assigned to treatment groups (n=6/group) on the basis of mass. Specifically, the heaviest bird was assigned to the first group, the next heaviest to the second group, and so on. During the 4-day pre-treatment period, all food was removed from the cages within 1 hour of light onset. Next, 2 cups, each containing 50 g of PFBC were placed in the front center of each cage. Cups were bound together with a rubber band to reduce spillage, and consumption was assessed after 2 hours. After testing, and until light onset of the following day, birds had free access to feed.

On the day following the last pre-treatment day, a 4-day treatment period began. Within 1 hour of light onset, each group was given 2 cups. One contained 50 g of PFBC thoroughly mixed with different concentrations of a candidate repellent. The other contained 50 g of plain PFBC. Cups were bound together with a rubber band, and cup positions were alternated daily. As in pre-treatment, consumption was measured after 2 hours. At the end of the fourth treatment trial, all birds were re-weighed to assess whether any change from pre-treatment mass had occurred.

The ratio of an individual's treatment to pretreatment consumption was taken as an index of relative repellency. A score of 1.0 indicated no difference between pretreatment and treatment food intake. A score of zero indicated complete rejection of the treated food. One-cup tests. The procedures detailed in Mason, J. R., et al., supra, (1989) for 1-cup avian repellency evaluations were followed. Briefly, for each candidate repellent, starlings were randomly selected, weighed, and then assigned to treatment groups (n=6/group) as described above. On the day following group assignment, a 4 day pre-treatment period began, identical in all respects to the 2-cup pre-treatment period, except that each bird was presented with only 1 cup containing 50 g of PFBC. A 4 day treatment period immediately followed pre-treatment, and during each treatment, each group was presented with 50 g samples of PFBC adulterated with a different amount of candidate repellent. Consumption was recorded after 2 hours. Birds had free access to plain PFBC and water during the night. At the end of the fourth treatment trial, all birds were reweighed.

The repellency scores were calculated in the same manner as for the two-cup tests.

Example 1

Development of a Structure-Activity Model
Acetophenones

Figure 1B:
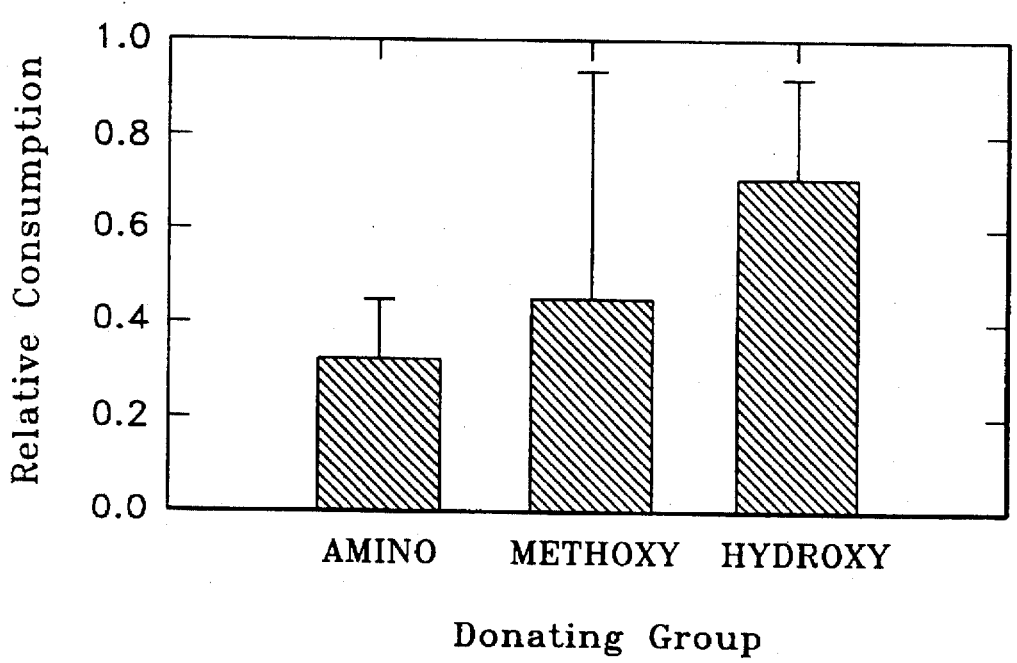
Figure 1C:
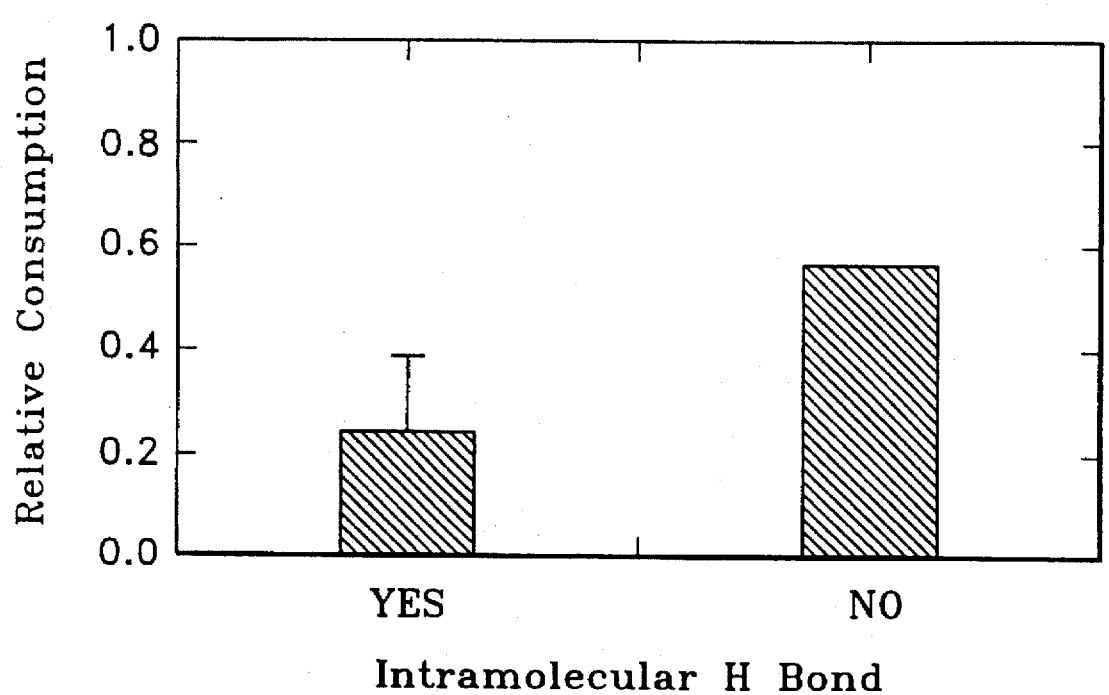

Summary: Isomers of three acetophenone moieties were studied to determine the contribution of isomeric position, electron donating group and intramolecular hydrogen bonding on repellency (FIG. 1). Repellency was evaluated using a standard dose-response assay for fluid intake. Several general molecular features contributed to repellency. First, not all acetophenones were repellent. Repellency was characterized by specific structural and electronic features. Second, molecules with intramolecular H-bonds were better repellents. Third, repellency was related to the electron donating capacity of the electron donating group, where capacity is ranked as amino>methoxy>hydroxy. Fourth, isomers were not all equally repellent, indicating that an empirical characterization of a molecule is an inadequate basis for evaluating repellency. For example, OAP is an order of magnitude more potent than its methoxy isomer (MAP), where potency was evaluated as the test concentration for which a 50% suppression of baseline consumption occurred (Table 1). The isomeric effect is even more pronounced when the electron donating effect is diminished, e.g. hydroxyacetophenone moieties. The ortho isomer (2HAP) is repellent, but the meta (3HAP) and para (4HAP) isomers are totally nonrepellent.

TABLE 1

Summary of repellency for Acetophenone moieties.

| Compound | Concentration (mM) at the 50% Repellency Level | Minimum Repel Repellency at 30 mM (the approximate water saturation limit) |
|---|---|---|
| 2-hydroxyacetophenone | 2.6 | 0.15 |
| 3-hydroxyacetophenone | infinity | 1.0 |
| 4-hydroxyacetophenone | infinity | 1.0 |
| 2-methoxyacetophenone | 2.6 | 0.1 |
| 3-methoxyacetophenone | 5.9 | 0.12 |
| 4-methoxyacetophenone | 1.8 | 0.05 |
| o-aminoacetophenone | 1.7 | 0.16 |
| 3-aminoacetophenone | 13.7 | 0.31 |
| 4-aminoacetophenone | 5.8 | 0.15 |

Discussion: When the electron donating amino group is in the ortho position, intramolecular hydrogen bonding between the carbonyl and amino group is possible. Electron sharing with the benzene ring is possible through resonance. When the amino group is in the meta position, no intramolecular hydrogen bonding is possible and electron sharing is primarily through induction. When the amino group is in the para position, there is still no intramolecular hydrogen bonding, but electron sharing is possible through resonance.

Methoxyacetophenones were selected because the methoxy group is less basic than the amino group and no intramolecular hydrogen bonding is possible for this molecule. Resonance effects are similar to the aminoacetophenones for each of the isomers. Hydroxyacetophenones were selected because they are the least basic of the acetophenone moiety series, but allow intramolecular hydrogen bonding when in the ortho position. The comparison of these moieties demonstrated the relative importance of intramolecular hydrogen bonding, basicity and resonance for avian repellency.

Example 2

Refinement of the Structure-Activity Model:
Benzoic Acid Derivatives

Summary: The generality of the structure-activity relationships derived from the Acetophenone Tests was made by evaluating dose-response profiles for a different class of compounds characterized by different physicochemical characteristics, e.g. benzoic acid derivatives. The results indicate several important trends (Table 2). First, not all aromatic compounds are repellent. Aromatic structures must possess certain specific structural and electronic properties to be repellent. Second, isomers do not have identical repellent properties, e.g. 2-aminobenzoic acid is repellent while the 3- and 4-position isomers are not repellent. Third, distortion of the pi electron cloud diminishes the repellent effect. Fourth, decreasing electron richness of the aromatic ring diminishes repellency. Fifth, of the compounds tested, only the amino isomeric substitutions showed repellent effects. In general, repellency is correlated to the general structural and electronic features identified in Example 1.

TABLE 2

Summary of Repellency for Benzoic Acid Derivatives.

| Compound | Concentration (in %) at the 50% Repellency Level | Minimum Repellency at 0.5% |
|---|---|---|
| benzoic acid | infinity | 1.0 |
| 2-aminobenzoic acid | 0.09 | 0.02 |
| 3-aminobenzoic acid | 0.28 | 0.66 |
| 4-aminobenzoic acid | 0.27 | 0.41 |
| 5-nitro-2-aminobenzoic acid | 0.90 | 0.68 |
| 2-methoxybenzoic acid | 0.24 | 0.64 |
| 3-methoxybenzoic acid | 0.03 | 0.74 |
| 4-methoxybenzoic acid | infinity | 1.0 |
| 2-hydroxybenzoic acid | 0.21 | 0.64 |
| anthranilamide | infinity | 0.48 |
| benzamide | infinity | 0.42 |
| o-carboethoxybenzene sulfonamide | infinity | 1.0 |
| 4-ketobenztriazine | 0.02 | 0.23 |

Discussion: Benzoic acids were chosen to examine the effects of increasing the acidity of molecules by replacing the carbonyl electron withdrawing group attached to the benzene ring with a carboxylic acid. The amino substitution for the electron donating group was chosen for examination because it represented a highly basic substituent. As was the case for acetophenone moieties, the ortho position in anthranilic acid is capable of intramolecular hydrogen bonding, while the meta and para isomers are not. Electron sharing with the benzene ring for these isomers is through resonance for the ortho and para isomers and induction for the meta isomer.

The methoxy and hydroxy moieties were chosen because they represented a less basic electron donating group than the amino substitution. 5-nitro anthranilic acid (5-nitro-2-aminobenzoic acid) was selected to increase the electron withdrawal from the phenyl ring. In this case intramolecular hydrogen bonding is still possible between the amino and carboxyl groups, though the electron sharing via resonance is more uniformly spread over the entire molecule.

By adding a nitro group to anthranilic acid (an otherwise good repellent), the addition of a strong withdrawing group was tested as to how it affected repellency (e.g. 5-nitro anthranilic acid). Examination of anthranilamide allowed testing of the effect of internally compensating the electron withdrawal capacity of the carboxyl group on repellency. The internal compensation for withdrawing capacity allows the donating amino group to contribute electrons to the phenyl ring. Examination of benzamide showed how internal compensation of the withdrawal groups and elimination of the donation group effects repellency. In this case, resonance within the phenyl ring is unaffected and the ring is relatively electron poor when compared to anthranilamide.

Previous work had shown that esters of benzoic acids are good repellents. The findings herein indicate that planarity of the pi cloud formation is also important for repellency. Examination of o-carboethoxybenzene sulfonamide showed how distortion of the pi cloud affects repellency. Isatoic anhydride was selected because the rigid planar structure is maintained via covalent bonds but the hetero ring is strongly withdrawing, thus making the phenyl ring electron poor. 4-ketobenztriazine was selected because it maintains a planar structure in the hetero ring, but donates electrons to the phenyl ring.

Of all the single substitutions of electron donating groups for benzoic acid derivatives, only the amino isomeric substitutions showed repellent effects. Consumption for all concentrations of benzoic acid, salicylic acid, and isomers of methoxy benzoic acid were all similar to pretreatment consumption levels ($P>0.05$). Consumption of water decreased as a function of increasing concentration for meta- and 4-aminobenzoic acid ($F=5.55$, $P=0.004$ and $F=3.59$, $P=0.021$, $df=5,17$, respectively). Anthranilic acid was the most effective repellent of the benzoic acid series ($F=24.29$, $P\ 0.001$, $df=5,17$). Post-hoc tests indicated consumption levels were similar for 0.5, 0.25 and 0.13% concentration and that consumption for this group differed from the control and 0.03 and 0.06% concentrations. Most striking was the magnitude of drinking suppression, nearing zero consumption for the highest concentrations tested.

Consumption did not differ from control levels for isatoic anhydride, o-carboethoxybenzene sulfonamide, 2-aminobenzamide, and 5-nitroanthranilic acid within the heterocyclic series ($P>0.05$). Consumption was not affected by isatoic anhydride or o-carboethoxybenzene sulfonamide ($P>0.05$). Only consumption for 4-ketobenztriazine showed any repellent effects ($F=8.19$, $df\ 5,30$, $P<0.001$). Only the highest concentration did not significantly differ from zero consumption, though reduced consumption was evident for concentrations as low as 0.05%.

Example 3

Test of the Predictions of the Structure-Activity Model: Aromatic Structures

Summary: A total of 45 compounds were evaluated for avian repellency. Prior to such evaluation, an a priori prediction was made whether the compound would be repellent or not using the guidelines set forth herein. The compounds were evaluated by measuring the amount of fluid (containing a candidate repellent) consumed, and comparing this intake to that observed for controls (birds consuming plain water). A compound was considered repellent if intake over a six hour period was statistically different relative to the control ($P<0.05$, indicated by an asterisk in the table). The probability criterion used is the accepted value used by scientists. Concentrations tested were similar for all candidate repellents, i.e. 5,000 ppm. Table 3 contains the chemical identity, the a priori expectation whether the chemical should be an avian repellent (+) or not (0), and the results of the evaluation of repellency.

The predictions of repellency were concordant with the experimental observations for 41 of the 45 chemicals evaluated. Assuming that there is a 50% chance of predicting repellent activity correctly (without a priori information on structure-activity relationships), the guidelines give a high probability of accurately identifying the likely activity of a candidate repellent ($z=5.52$, $P<0.001$).

TABLE 3

| Chemical Identity | Prediction | Evaluated Repellency |
|---|---|---|
| acetophenone | + | repellent |
| 2-amino-4,5-dimethoxyacetophenone | + | repellent |

TABLE 3-continued

| Chemical Identity | Prediction | Evaluated Repellency |
|---|---|---|
| 2-amino-4-5-dimethoxy benzoic acid | 0 | nonrepellent |
| methyl-2-methoxybenzoate | + | repellent |
| methyl-4-methoxybenzoate | + | repellent |
| methyl benzoate | + | repellent |
| sodium benzoate | 0 | nonrepellent |
| anthranil | + | repellent |
| acetyl salicylic acid | 0 | nonrepellent |
| 2-aminobenzyl alcohol | + | repellent |
| N,N-dimethyl aniline | + | repellent |
| 2-amino sulfonic acid amine | 0 | nonrepellent |
| beta alanine | 0 | nonrepellent |
| methyl ester of betha alanine | 0 | nonrepellent |
| methyl cinnamate | 0 | nonrepellent |
| phenyl ethyl acetate | 0 | nonrepellent |
| anethole | 0 | nonrepellent |
| ethyl butyrate | 0 | nonrepellent |
| citral | 0 | nonrepellent |
| cinnamyl aldehyde | 0 | nonrepellent |
| ethyl phenyl acetate | + | repellent |
| methyl phenyl acetate | + | repellent |
| ethyl cinnamyl acetate | 0 | nonrepellent |
| benzyl acetate | 0 | nonrepellent |
| cinnamyl alcohol | + | repellent |
| phenethyl alcohol | + | repellent |
| benzaldehyde | + | repellent |
| phenyl acetalaldehyde | 0 | nonrepellent |
| hydrocinnamaldehyde | 0 | nonrepellent |
| benzophenone | 0 | nonrepellent |
| salicylaldehyde | + | repellent |
| o-tolualdehyde | + | repellent |
| o-anisaldehyde | + | repellent |
| pyrole | + | repellent |
| pyridine | + | repellent |
| pyrazine | + | repellent |
| indol | + | repellent |
| piperazine | + | repellent |
| isoquinoline | + | repellent |
| benzothiole | + | repellent |
| 5,6,7,8-tetrahydro-isoquinoline | + | repellent |
| 2-acetyl thiazole | + | repellent |
| 2-acetyl thiophene | + | repellent |
| thiazole | + | repellent |
| tetrahydroquinoline | + | repellent |

Example 4

Detailed Characterization of Other Benzene Structures

Summary: Other benzene structures were evaluated for repellency in view of the structure-activity relationships illuminated in Examples 1 and 2. Standard drinking assays were used for the evaluation process. The general features of the structure-activity model were confirmed (Table 4). First, isomers were not equal in their repellent effect, e.g. 2-methoxybenzoate was a more potent repellent than its 4-methoxy isomer. Second, the aromatic ring is critical to repellency, e.g. beta-alanine and the methyl ester of beta-alanine are analogous nonaromatic structures to methyl anthranilate and dimethylanthranilate, yet they are not repellent. Third, the electron richness of the aromatic structure is important. Fourth, the acidic function of the electron withdrawing group is important. Acidity in the electron withdrawing substituent tends to hinder repellency. Fifth, stearic effects and extreme delocalization of lone pairs of electrons (as occurs with meta isomers and aromatics multiply substituted with electron withdrawing groups) interferes with repellency. Sixth, repellency of the structures identified by the structure-activity model do not operate via conditioned learning, rather the mechanism for repellency is an unlearned avoidance response, mediated via sensory irritation of the trigeminal nerve.

TABLE 4

Summary of Repellency Characteristics of Other Benzene Ring Structures.

| Compound | Concentration (mg/L) at the 50% Repellency Level[a] | Minimum Repellency at 5000 mg/L[b] |
|---|---|---|
| methyl-2-methoxybenzoate | 2013 | 0.15 |
| methyl-4-methoxybenzoate | 107 | 0.82 |
| methyl benzoate | 554 | 0.61 |
| sodium benzoate | infinity | 1.0 |
| 2-amino-4,5-dimethoxyacetophenone acetophenone | 170 | 0.26 |
| acetophenone | 536 | 0.35 |
| 2-amino-4,5-dimethoxybenzoic acid | infinity | 1.0 |
| acetylsalicylic acid | 1429 | 0.53 |
| anthranil | 636 | 0.06 |
| 2-aminobenzyl alcohol | 435 | 0.25 |
| N,N-dimethylaniline | 827 | 0.36 |
| 2-aminobenzene sulfonic acid | infinity | 1.0 |
| methyl salicylate | 561 | 0.40 |
| cinnamide | 93 | 0.60 |
| methyl ester of beta-alanine | 3416 | 0.63 |
| beta-alanine | infinity | 1.0 |

Example 5

Further Characterization of Other Aromatic Structures

Summary: Conjugated forms of non-benzene aromatic structures were identified as likely repellents using the criteria established in Examples 1–3 and tested. Assays were standard drinking assays and compounds were tested at an equivalent of 5000 mg/L. All compounds proved to have repellent properties (Table 5). The best repellents are those possessing an aromatic structure and a heterocyclic ring, e.g., isoquinoline, indole, tetrahydroquinoline, 5,6,7,8-tetrahydroisoquinoline, and benzothiole. Compounds with N in the aromatic structure were less effective than thiole or phenyl structures. Aromatic structures with conjugated substituent groups or were also good repellents, e.g., 2-acetylthiophene and 2-acetylthiazole. The saturated ring structure, piperazine, was not among the best repellents.

TABLE 5

Summary of Repellent Characteristics for Other Aromatic Compounds.

| Compound | Repellency at 5000 mg/L |
|---|---|
| isoquinoline | 0.08 |
| 2-acetylthiophene | 0.08 |
| tetrahydroquinoline | 0.10 |
| benzothiole | 0.15 |
| indole | 0.16 |
| pyridine | 0.23 |
| 5,6,7,8-tetrahydroisoquinoline | 0.23 |
| 2-acetylthiazole | 0.34 |
| thiazole | 0.35 |
| pyrole | 0.35 |
| piperazine | 0.48 |
| pyrazine | 0.55 |

Example 6

Further Characterizations of Acetates

Summary: Acetates have been postulated as having repellent properties (Crocker and Perry, 1990) on the basis that some aromatic esters, e.g. anthranilates are bird repellents. Random selection and testing (using standard drinking assays) of common acetates reveals several patterns. First, not all aromatic compounds are repellent. Second, acetates are poor repellents. These results are not surprising in light of Examples 1–3. The aromatic substituents of the tested acetates are not planar to the pi electron cloud. Thus, repellency is sterically hindered for this group of compounds.

TABLE 6

Summary of Repellent Characteristics for Acetates

| Compound | Minimum Repellency at 5000 mg/L |
|---|---|
| benzyl acetate | 0.41 |
| ethyl cinnamate | 0.46 |
| methyl phenylacetate | 0.46 |
| ethyl phenylacetate | 0.54 |
| phenyl ethylacetate | 0.73 |
| methyl cinnamate | 1.0 |

Example 7

Further Characterizations of Aldehydes

Summary: Several simple aldehydes were selected for testing using the standard drinking assay. Several trends were observed. First, not all aromatic aldehydes were repellent. Second, non-conjugated aldehydes were poor repellents, e.g., phenylacetylaldehyde. This is consistent with the structure-activity prediction that only conjugated substituents should be good repellents. Third, the double bonds within the alkene substituent, e.g., hydrocinnamaldehyde, minimized stearic hinderance effects.

TABLE 7

Summary of Repellent Characteristics for Aldehydes.

| Compound | Minimum Repellency at 5000 mg/L |
|---|---|
| benzaldehyde | 0.09 |
| o-anisaldehyde | 0.17 |
| o-tolualdehyde | 0.28 |
| hydrocinnamaldehyde | 0.31 |
| o-salicaldehyde | 0.33 |
| phenylacetylaldehyde | 0.85 |
| benzophenone | 1.0 |

Example 8

Confirmation of the Structure-Activity Model: Aminoacetophenones

Summary: Repellent effects of aminoacetophenones were evaluated in feeding trials using standard feeding assays. 2-Cup tests approach the sensitivity of drinking tests. The ranking of repellency for each of the assays was consistent with the drinking assays. Ortho and para isomers were better repellents than the meta isomer. Higher concentrations of repellent were needed in feeding trials to produce the same effect as found in drinking trials.

TABLE 8

Summary of Repellency for Aminoacetophenone Feeding Trials.

| Compound[1] | Repellency: 2-cup | Repellency: 1-cup |
|---|---|---|
| o-aminoacetophenone | 0.13 | 0.46 |
| alpha-aminoacetophenone | 0.25 | 0.39 |
| 3-aminoacetophenone | 0.22 | 0.80 |
| 4-aminoacetophenone | 0.14 | 0.66 |

[1]All compounds reported here were evaluated at 1% (g/g).

Example 9

Confirmation of the Structure-Activity Model: Vanillin Derivatives

Summary: Vanillin derivatives were evaluated for their repellent effect using standard feeding assays. Several recurrent trends emerged. First, not all aromatic compounds are repellent. Only those with structural and electronic characteristics consistent with those delineated with the model showed good repellent activity. Second, compounds with long chain substituents were not repellent, e.g. casaicin and methyl capsaicin. This is consistent with the model's prediction that stearic hinderance will decrease repellency. Third, compounds with two methoxy groups as electron donating substituents, e.g. veratryl alcohol, veratryl acetamide, veratryl amine, were better repellents that those with hydroxy groups, e.g. vanillyl alcohol and vanillyl acetamide. Fourth, compounds known to be repellent to mammals, i.e. capsaicin and methyl capsaicin are not repellent to birds. This is consistent with observations that the bird repellents identified are generally not repellent to mammals, indicating different sensory worlds between birds and mammals as to the character of a chemoirritant.

TABLE 9

Summary of Repellency for Vanillin Derivatives.

| Compound | Concentration (%) | Repellency: 2-cup | Repellency: 1-cup |
|---|---|---|---|
| vanillin | 1.7 | 0.05 | 0.88 |
| vanillyl alcohol | 1.7 | 0.22 | 1.00 |
| veratryl alcohol | 1.9 | 0.06 | 0.20 |
| capsaicin | 1.0 | — | 1.00 |
| methyl capsaicin | 1.0 | — | 0.75 |
| vanillyl acetamide | 1.0 | — | 1.00 |
| veratryl amine | 1.0 | — | 0.13 |
| veratryl acetamide | 1.0 | — | 0.13 |

Example 10

Confirmation of the Structure-Activity Model: Coniferyl Benzoate Derivatives

Summary: Coniferyl benzoate derivatives were evaluated for their repellent effect using standard feeding assays. Several recurrent trends emerged. Compounds with a hydroxy attached directly to the benzene ring or the alpha carbon were characterized by lower repellency. This is consistent with the repellent detracting effects of relatively acidic functions found either in the electron donating or withdrawing groups. The more basic methoxy substituent substitutions were characteristically better repellents.

TABLE 10

Summary of Feeding Repellency for Coniferyl Benzoate Deriatives.

| Compound | Concentration (%) | Repellency: 2-cup | Repellency: 1-cup |
|---|---|---|---|
| benzoic acid | 1.38 | 0.67 | 0.37 |
| coniferyl benzoate | 1.60 | 0.50 | 0.89 |
| cinnamyl benzoate | 1.34 | 0.33 | 0.56 |
| coniferyl alcohol | 1.01 | 0.17 | 0.71 |
| cinnamyl alcohol | 1.52 | 0.13 | 0.64 |
| 3,4-dimethoxycinnamylbenzoate | 1.68 | 0.25 | 0.40 |
| 3,4-dimethoxycinnamyl alcohol | 1.09 | 0.06 | 0.33 |

Example 11

Anthranilatic Esters as water repellents

Example 11a

Wastewater

Procedure.

Birds.—Adult European starlings (*Sturnus vulgaris*) were decoy-trapped and transported to the laboratory. Upon arrival, the birds were individually caged (61×36×41 cm) under a 12:12 light:dark: cycle with light onset at 0700 h. Food was available ad libitum. Before experiments began, the birds were permitted free access to tap water.

One-choice Tests.—Starlings were given 3 days of pretreatment during which water consumption was measured for 6 hr. At the end of this period, individuals whose variance about the 3 day mean consumption was greater than ± one standard deviation of the population variance were excluded from the trials. Those birds with stable daily water consumption were ranked according to mean water consumption and assigned to treatment groups. The bird with the highest water consumption was assigned to the deionized, distilled water treatment group, the bird with the second highest consumption was assigned to the leachate pond-water treatment, the bird with the third highest consumption was assigned to the MA+deionized, distilled water treatment and the bird with the fourth highest consumption was assigned to the MA+leachate pond-water group, and so forth, until all birds were assigned to a group. (MA concentration 0.5% v/v)

After assignment to a treatment group a 1 day drinking trial began. Birds had free access to feed and tap water during the night. Beginning at 0930, the water was replaced with preassigned concentrations of chemicals and consumption was recorded every 2 hours for the next 6 hours. After the test, birds were given free access to tap water. Consumption of tap water was monitored overnight and that of deionized, distilled water the next day, and these values were compared with pretreatment drinking to determine whether consumption had returned to normal. There were no mortalities, and at the end of all experiments birds were released to the wild.

Analysis.—There were no differences of mean consumption of deionized, distilled water among groups during the pretreatment period. All data were found to be homogeneous unless otherwise noted. Data were analyzed using a one-way analysis of variance (ANOVA) with the main effect as treatment group. Post-hoc differences were determined using a Scheffe's test.

Figure 2:
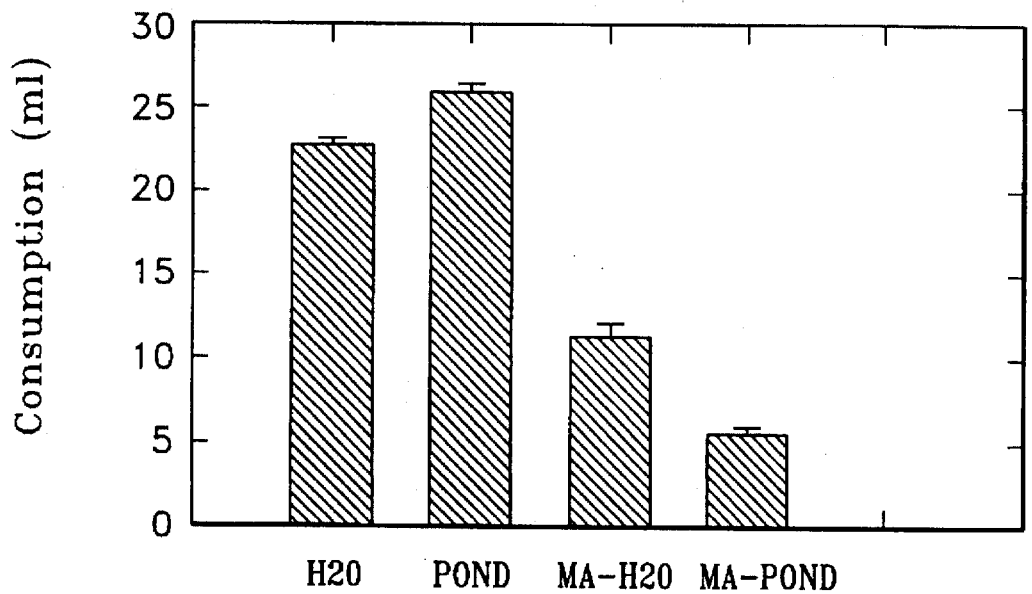
FIG. 2. Laboratory drinking trials for European starlings. N=9 birds per experimental group. During testing birds were given: deionized, distilled water ($H_2O$), water from cyanide holding ponds with cyanide removed (Pond), deionized, distilled water treated with MA (MA-$H_2O$), and pond water treated with MA (MA-Pond).

Results.—There was a significant treatment effect (FIG. 2, F=23.8, df=3,68, P<0.001). All treatments differed from one another at the P<0.05 level. Birds consumed significantly more pond-water than any other type of water. Next, birds consumed high levels of deionized, distilled water. Addition of MA to the deionized, distilled water reduced consumption of water to one-half the untreated level. Surprisingly, addition of MA to wastewater decreased consumption to levels statistically indistinguishable from zero consumption (P<0.05). This dramatic reduction indicates a synergism between MA and the non-potable water.

Example 11b

Fresh Water Field Trials

Procedure.

Birds.—Sixteen mallards (*Anas platyrhincus*) and 16 ring-billed gulls (*Larus delawarensis*) were funnel or rocket trapped and kept two birds/species to a pen. Pens were 8×4 m corrals, each with an attached 2.5×2.5×2.5 m shaded holding pen. Pens were set up on mowed grass in an area isolated from human disturbance. Each corral had 2, 0.8 m diameter or 2, 1.0 m diameter plastic pools filled with 40 L or 90 L, of water (10–12 cm deep), respectively. For each of 2 days, 2 mallards, with primary feathers pulled on 1 wing to prevent flying, were placed in each holding pen and released daily for 9 hrs into the corral to acclimate to the test condition. Each corral contained a pan with cracked corn, millet and commercial duck food.

Treatments.—On test day 1 at 0800, 2 formulations of MA embedded in a polymer were applied to fresh water (0.5% w/v) in a randomly selected pool in each corral. Formulation 1 contained 16% MA and was applied to the pool as 1 part formulation to 200 parts water, yielding 0.08% concentration of active ingredient in the pool. Formulation 2 consisted of 64% MA applied to the pool as 1 part formulation to 200 parts water, yielding a concentration of 0.32% active ingredient. Water depth was measured to the nearest ml and the 2 mallards were released into the corral. One of 4 observers (2 corrals per observer) watched each corral for 120 20-sec intervals (40 min total) over the next 2 hours. The observer recorded the number of mallards in each pool (pool use) during each 20-sec interval and the total number of times a bill touched the water (i.e. drinking or bathing activity) for each pool. At 1600 the water depth was remeasured and the mallards were returned to their holding pen where they were provided with food, but no water. This routine was maintained on days 2, 3, and 4. The mallards were kept in their holding pens on day 5 (with drinking water and food). On day 6, they were released into corrals with only the MA-treated pool available. The birds were observed as before and the experiment was then terminated.

For the gull experiment the methods were the same as for mallards, except that the tests took place in the holding pens (the gulls could fly) and only 1 formulation (#2) of MA was used. The gulls were fed fresh fish daily. Four pens were used.

Analysis.—Data were analyzed using a repeated measures analysis of variance with days as the repeated measure.

Figure 3:
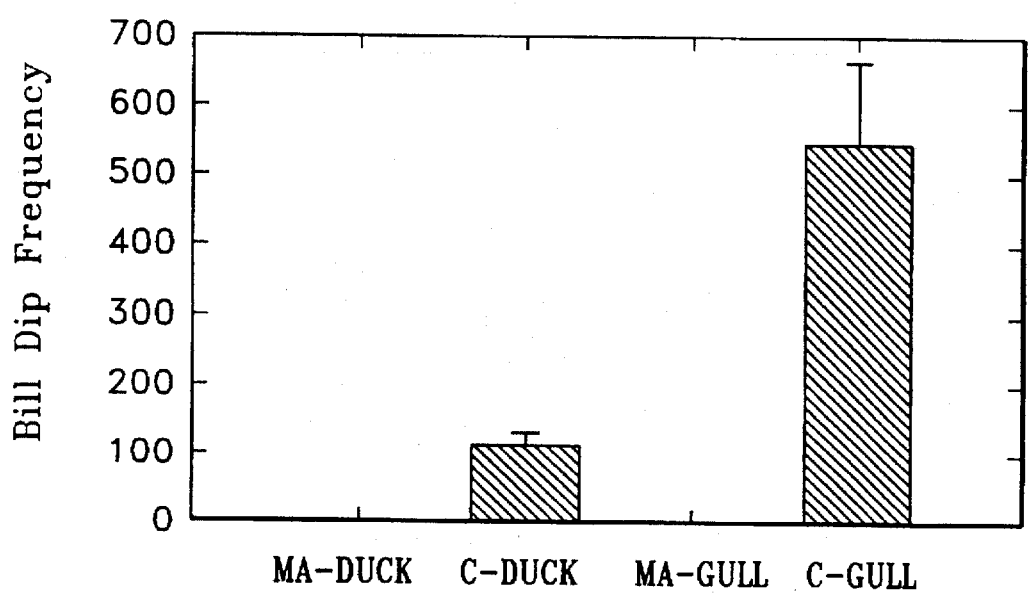
FIG. 3. Frequency of drinking behavior for treated (MA) and untreated (C) pools for ducks and gulls. For ducks, the data reflect the combined frequency for both formulations of MA.
Figure 4:
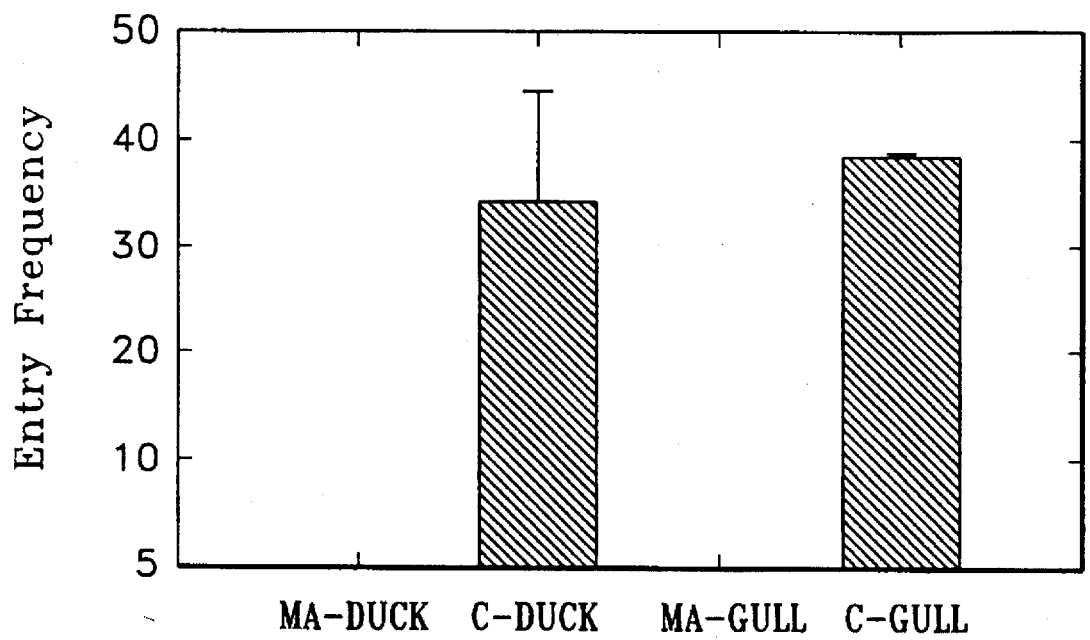
FIG. 4. Frequency of entry into treated (MA) and untreated (C) pools for ducks and gulls. For ducks, the data depicted reflect the combined frequency for both formulations of MA.

Results.—Both formulations of MA were effective in the duck experiment at keeping mallards from swimming, or bathing in MA-treated pools (FIG. 4, F=46.1, P<0.001 and F=12.5, P<0.01, df=1,3 for formulations 1 and 2, respectively). Both formulations were also effective at inhibiting drinking and bill dipping behavior by ducks (FIG. 3, F=47.1, P<0.01 and F=42.9, P<0.01, df 1,3 for formulations 1 and 2, respectively). During the 4 days of the 2-choice test 98.5% of the entries into pools by ducks and 96.1% of bill contacts were in the untreated pools. In the 1-choice test, where ducks were only exposed to pools treated with MA, use of the pools for entries and drinking was restricted to 96.2% and 91.2% relative to pretreatment levels respectively.

Repellency was even more pronounced in the gull experiments (FIGS. 3 and 4). During the 2-choice tests for formulation 2, over 99% of entries and bill contacts were in the untreated pools (F=61.2, P<0.01 and F=55.7, P0.01, df=1,3 for swimming and bill dips, respectively). For the 1-choice tests, only a single incidence of pool use and 83 bill contacts were recorded compared with a daily means of 38.8 and 552.9 for fresh water during the previous four days.

The concentrations of MA in the formulations in Example 11b corresponded to 0.08 and 0.32%. These values are substantially lower than effective dosages reported for feeding trials in the laboratory. These tests demonstrate the applicability of laboratory data to water repellency in field situations.

We claim:

1. A method for repelling birds from consuming or utilizing a material otherwise susceptible to consumption or utilization by birds consisting essentially of providing a compound having an aromatic core structure characterized by one of the following core ring structures

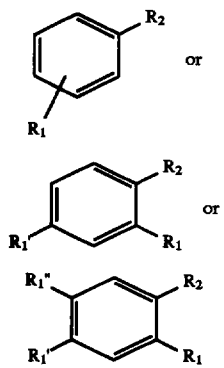

wherein $R_1$ or $R_{1'}$ or $R_{1''}$ is an electron donating group and $R_2$ is an electron withdrawing group or a neutral group which group does not substantially hinder electron donation to the core ring structure by $R_1$ to said material in an amount sufficient to reduce consumption of said material by at least about fifty percent, provided that said compound is not an anthranilic ester or an ester of phenylacetic acid.

2. A method for identifying compounds for repelling birds from consuming or utilizing a material otherwise susceptible to consumption or utilization by birds consisting essentially of the following steps: a) selecting a compound having an aromatic core structure characterized by one of the following core ring structures

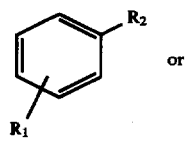

-continued

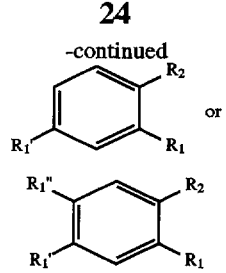

wherein $R_1$ or $R_{1'}$ or $R_{1''}$ is an electron donating group and $R_2$ is an electron withdrawing group or a neutral group which group does not substantially hinder electron donation to the core ring structure by $R_1$; and b) testing said compound for repellency by comparing (i) the consumption or utilization by a bird of a material with (ii) the consumption or utilization by a bird of the same material to which an avian repellent compound selected according to step a) has been added, whereby a reduction in consumption of at least about fifty percent as compared to the amount which would be consumed or utilized by said birds in the absence of said compound represents repellency.

3. The method of claim 1 or 2 wherein $R_2$ is an electron withdrawing group.

4. The method of claim 1 or 2 wherein $R_2$ is group capable of forming a hydrogen bonded ring structure with an electron donating group.

5. The method of claim 1 or 2 wherein the electron donating groups, $R_1$ or $R_{1'}$ or $R_{1''}$, contribute electrons to the core ring structure.

6. The method of claim 1 or 2 wherein the electron donating group $R_1$, contributes electrons to the core ring structure in the positions 2, 3 or (4) with respect to $R_2$.

7. The method of claim 1 or 2 wherein the electron donating group is basic.

8. The method of claim 1 or 2 wherein the substituents on $R_2$ are of the type that do not substantially prevent $R_1$, from donating electrons to the core ring structure.

9. The method of claim 1 or 2 wherein there is intramolecular hydrogen bonding between $R_1$ and $R_2$ when $R_1$ is in position 2 relative to $R_2$.

10. The method of claim 1 or 2 wherein $R_1$ and $R_2$ comprise a heterocyclic ring attached to the core ring structure.

11. The method of claim 1 or 2 wherein $R_2$ is a lower acyl, nitro, carboxylic acid or ester.

12. The method of claim 1 or 2 wherein the electron donating group is selected from the group consisting of amine, o-lower alkyl, N-lower alkyl, and N-di lower alkyl.

13. A method of repelling birds from consuming or utilizing a material otherwise susceptible to consumption or utilization by birds consisting essentially of the following steps: a) selecting at least one compound from the group consisting of alpha-aminoacetophenone, ortho-aminoacetophenone, meta-aminoacetophenone, para-aminoacetophenone, ortho-hydroxyacetophenone, ortho-methoxyacetophenone, meta-methoxyacetophenone, para-methoxyacetophenone, 3-aminobenzoic acid, 4-aminobenzoic acid, 4-ketobenztriazine, coniferyl benzoate, cinnamyl benzoate, 3-4-dimethoxycinnamyl benzoate, coniferyl alcohol, cinnamyl alcohol, 3-4-dimethoxycinnamyl alcohol, acetophenone, 2-amino-4,5-dimethoxyacetophenone, methyl-2-methoxybenzoate, methyl-4-methoxybenzoate, methyl benzoate, anthranil, 2-aminobenzyl alcohol, N,N-dimethyl aniline, ethyl phenyl acetate, methyl phenyl acetate, phenathyl alcohol, benzaldehyde, salicylaldehyde, o-tolualdehyde, o-anisaldehyde, pyrole, pyridine, pyrazine, indol, peperazine, isoquinoline, benzothiole, 5,6,7,8-tetrahydroisoquinoline, 2-acetyl thiazole, 2-acetyl thiophene, thiazole, and tetrahydroquinoline; and b) providing an avian repellent amount of said compound to said material.

14. The method according to claim 13 wherein said compound is provided to said material with a liquid carrier.

15. The method according to claim 13 wherein said compound is provided to said material with a vehicle comprising a starch, oil or polymer which at least partially encapsulates or emulsifies the compound.

16. The method according to claim 15 wherein said material is an edible and said vehicle and compound are dispersed throughout said edible.

17. The method according to claim 13 wherein said material is a liquid and said compound is dispersed in said liquid.

18. The method according to claim 13 wherein said water is non-potable water.

19. The method according to claim 13 wherein said material is a bird edible.

20. The method according to claim 13 wherein said amount of said compound is that amount sufficient to reduce consumption or utilization of said material by said birds by at least about ninety percent as compared to the amount of said material which would be consumed or utilized by said birds in the absence of said compound.

21. A method for repelling birds from consuming or utilizing non-potable water consisting essentially of providing at least one anthranilic ester selected from the group consisting of methyl anthranilate and dimethyl anthranilate to said non-potable water in an amount sufficient to reduce consumption of said non-potable water by at least about fifty percent as compared to the amount of said non-potable water which would be consumed or utilized by said birds in the absence of said compound.

22. The method according to claim 21 wherein said compound is provided to said non-potable water with a vehicle comprising a starch, oil or polymer which at least partially encapsulates or emulsifies said compound.

23. The method according to claim 21 wherein said amount of said compound is that amount sufficient to reduce consumption or utilization of said non-potable water by said birds by at least about ninety percent as compared to the amount of said non-potable water which would be consumed or utilized by said birds in the absence of said compound.

24. The method of claim 18 wherein said non-potable water is selected from the group consisting of free standing water on airport runways, free standing water on parking lots, industrial waste water, agricultural waste water, and water from mine tailing ponds.

25. The method of claim 21 wherein said non-potable water is selected from the group consisting of free standing water on airport runways, free standing water on parking lots, industrial waste water, agricultural waste water, and water from mine tailing ponds.

* * * * *